United States Patent [19]

Schmerling

[11] 4,046,819

[45] Sept. 6, 1977

[54] ALKYLATION OF ALKYL, CYCLOALKYL AND ARALKYL HALIDES

[75] Inventor: Louis Schmerling, Riverside, Ill.

[73] Assignee: UOP Inc., Des Plaines, Ill.

[21] Appl. No.: 682,550

[22] Filed: May 3, 1976

Related U.S. Application Data

[63] Continuation-in-part of Ser. No. 489,868, July 18, 1974, abandoned, which is a continuation-in-part of Ser. No. 247,082, April 24, 1972, abandoned.

[51] Int. Cl.² .............. C07C 19/00; C07C 23/10; C07C 25/14
[52] U.S. Cl. .............. 260/648 R; 260/653.1 R; 260/653.1 T; 260/658 C; 260/651 R
[58] Field of Search .............. 260/653.1 R, 653.1 T, 260/658 C, 648 R, 651 R

[56] References Cited

U.S. PATENT DOCUMENTS

| | | | |
|---|---|---|---|
| 2,058,466 | 10/1936 | Kharasch | 260/663 |
| 2,404,927 | 7/1946 | Schmerling et al. | 260/658 C |
| 2,418,832 | 4/1947 | Hanford et al. | 260/658 C |
| 2,434,289 | 1/1948 | Schmerling | 260/658 C |
| 2,440,800 | 5/1948 | Hanford | 260/658 C |
| 2,440,801 | 5/1948 | Hanford et al. | 260/663 |
| 2,533,052 | 12/1950 | Schmerling | 260/648 |
| 2,985,690 | 5/1961 | Miller | 260/653.1 T |
| 3,592,866 | 7/1971 | Magoon | 260/658 C |
| 3,641,171 | 2/1972 | Spooncer | 260/648 R |

FOREIGN PATENT DOCUMENTS

| | | | |
|---|---|---|---|
| 581,899 | 10/1946 | United Kingdom | 260/648 R |

*Primary Examiner*—Delbert E. Gantz
*Assistant Examiner*—J. Thierstein
*Attorney, Agent, or Firm*—James R. Hoatson, Jr.; Raymond H. Nelson; William H. Page, II

[57] ABSTRACT

Alkyl, cycloalkyl or aralkyl halides may be alkylated by treatment with an olefin in the presence of a catalyst comprising a free-radical generating compound such as an organic peroxide and also in the presence of a promoter comprising hydrogen chloride, said alkylation reaction being effected at temperatures at least as high as the decomposition temperature of the free-radical generating compound, to prepare alkylated halide-containing compounds.

12 Claims, No Drawings

ALKYLATION OF ALKYL, CYCLOALKYL AND ARALKYL HALIDES

CROSS-REFERENCE TO RELATED APPLICATIONS

This application is a continuation-in-part of my copending application Ser. No. 489,868 filed July 18, 1974, now abandoned, which is a continuation-in-part of my copending application Ser. No. 247,082 filed Apr. 24, 1972 and now abandoned, all teachings of which are specifically incorporated herein by reference thereto.

BACKGROUND OF THE INVENTION

Heretofore the prior art has shown that hydrogen bromide will add to an olefin compound in the presence of an organic peroxide to form an alkyl halide contrary to Markownikoff's rule. Likewise, the prior art as exemplified by U.S. Pat. Nos. 2,418,832 and 2,440,801 has shown a telomerization reaction in which recurring alkylaromatic or alkyl radicals may be prepared according to the equations set forth hereinafter.

$$ROOR \xrightarrow{\Delta} 2RO\cdot$$

$$RO\cdot + HCl \rightarrow ROH + Cl\cdot$$

$$Cl\cdot + C=C \rightarrow ClC-C\cdot$$

$$ClC-C\cdot + n-C=C \rightarrow ClC-C-(C-C)n\cdot$$

$$ClC-C-(C-C)_n\cdot + HCl \rightarrow ClC-C-(C-C)_nH + Cl\cdot$$

The Cl· atom starts a new chain as in the third equation. It is shown in these U.S. patents that when hydrogen chloride and ethylene are reacted, the product will comprise n-alkyl chlorides containing from 2 to 20 carbon atoms and more, said products being formed in approximately equal amounts of 5% to 9% while higher alkyl halides comprise about 40% of the product, the average composition of this material being calculated to be $C_{33}H_{67}Cl$. The hydrogen chloride reacts with a large number of molecular proportions of ethylene. However, this mechanism does not involve prior formation of alkyl chloride by the addition of hydrogen chlorides to the olefin. In contradistinction to this, in the process of the present invention the principal halide produced is one containing chiefly one (or, occasionally, two) olefin units per molecule of the alkyl halide undergoing reaction and the hydrogen chloride is present as a promoter, very little, if any, being converted to reaction product.

Another prior art method as set forth in U.S. Pat. Nos. 2,404,927 and 2,434,289 teaches the alkylation of alkyl halides using a Friedel-Crafts metal halide and particularly aluminum chloride for the reaction of alkyl halides and olefins. However, a free-radical generating catalyst such as an organic peroxide is definitely not present in the reaction mixture. This prior art reaction is acid-catalyzed and involves a carbonium ion mechanism while in contradistinction to this, as will hereinafter be shown in greater detail, the reaction of the present application is peroxide-initiated and involves the generation of free radicals. For example, the product which is obtained by the reaction of isobutyl chloride with ethylene in the presence of aluminum chloride is 1-chloro-3,3-dimethylbutane and may be illustrated by the following equations.

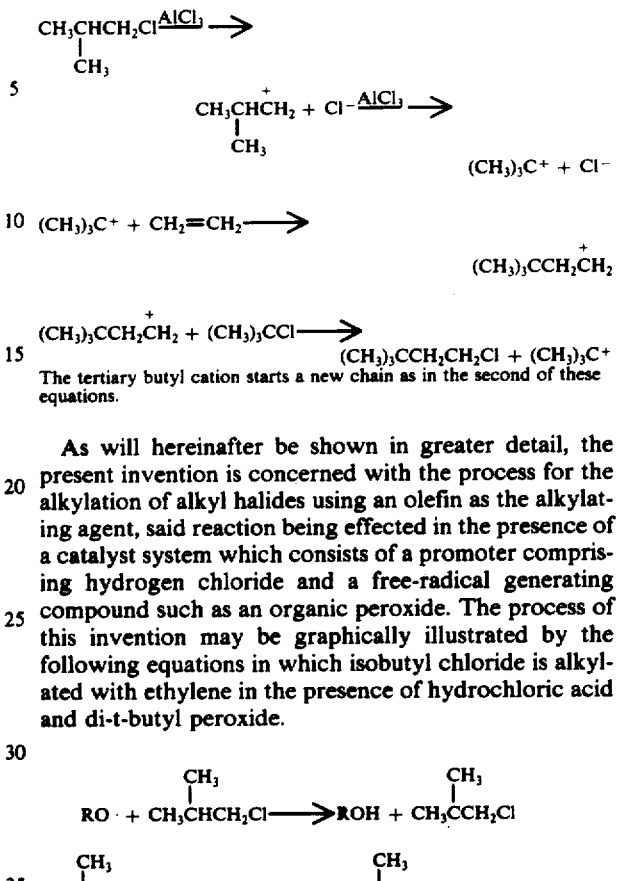

The tertiary butyl cation starts a new chain as in the second of these equations.

As will hereinafter be shown in greater detail, the present invention is concerned with the process for the alkylation of alkyl halides using an olefin as the alkylating agent, said reaction being effected in the presence of a catalyst system which consists of a promoter comprising hydrogen chloride and a free-radical generating compound such as an organic peroxide. The process of this invention may be graphically illustrated by the following equations in which isobutyl chloride is alkylated with ethylene in the presence of hydrochloric acid and di-t-butyl peroxide.

$$RO\cdot + CH_3\underset{\underset{CH_3}{|}}{C}HCH_2Cl \rightarrow ROH + CH_3\underset{\underset{CH_3}{|}}{\overset{\cdot}{C}}CH_2Cl$$

$$CH_3\underset{\underset{CH_3}{|}}{\overset{\cdot}{C}}CH_2Cl + CH_2=CH_2 \rightarrow CH_3\underset{\underset{CH_3}{|}}{\overset{|}{C}}CH_2Cl \atop \overset{|}{C}H_2CH_2\cdot$$

$$CH_3\underset{\underset{CH_3}{|}}{\overset{|}{C}}CH_2Cl + HCl \rightarrow CH_3\underset{\underset{CH_3}{|}}{\overset{|}{C}}CH_2Cl + Cl\cdot \atop \overset{|}{C}H_2CH_3$$

$$Cl\cdot + CH_3\underset{\underset{CH_3}{|}}{C}HCH_2Cl \rightarrow CH_3\underset{\underset{CH_3}{|}}{\overset{\cdot}{C}}CH_2Cl + HCl$$

The radical product of the last equation will start a new chain as in the second equation.

These equations account for the production of 1-chloro-2,2-dimethylbutane as the major reaction product. Abstraction of hydrogen from the first or third carbon atom of the isobutyl chloride will result in the formation of 3-chloro-2-methylpentane and 1-chloro-2-methylpentane respectively, while reaction of the chlorohexyl radicals with ethylene rather than with hydrogen chloride will lead to the formation of chlorooctanes. It will be noted that peroxide-induced reaction of isobutyl chloride with ethylene in the presence of hydrogen chloride yields chlorohexanes which are different from the isomer obtained in the presence of aluminum chloride as the catalyst. It is furthermore very important to note that little or no peroxide-induced alkylation occurs in thee absence of hydrogen chloride (compare Example II below).

It is evident from a review of the prior art that said art has taught the preparation of telomers by reaction of alkyl chlorides. However, in contradistinction to the process of the present invention, the prior art has not taught that a 1:1 adduct of olefin and hydrogen chloride could be formed as the principal product of the reaction, said adduct being present in the prior art in a relatively minor amount. This is evident from Example III of U.S. Pat. No. 2,440,801 which shows that n-alkyl chlorides ranging from butyl chloride to n-eicosyl chloride plus even longer chain chlorides were obtained when patentee reacted ethylene with hydrochloric acid in the presence of a peroxide. This reaction was carried out at relatively high pressures ranging from about 400 to 500 atmospheres. The results which are obtained in this reaction differ from the results which are obtained when utilizing the conditions and the hydrogen chloride and the halide reactant of the present invention. For example, when the reaction conditions of the present invention are employed, n-butyl chloride yields branch chained hexyl chlorides as the major products in place of the host of straight chained high molecular weight alkyl chlorides which were obtained by the prior art method. The patent differs in two important areas regarding the reaction from that of the present application. For example, the patentee does not begin with an alkyl radical so that telomerization of the ethylene with hydrogen chloride is the primary reaction and the intermediate chloroalkyl radicals abstract a hydrogen atom from the hydrogen chloride to yield the high molecular weight chlorides. The difference between the reaction set forth in the prior art patent and the present application is clearly indicated by the hereinbefore set forth equations and therefore the chain propagation step of the patent differs from the steps of the present application.

This invention relates to a proces for the alkylation of organic halides. More specifically the invention is concerned with a process for the alkylation of monohaloalkanes, monohalocycloalkanes, and aralkyl monohalides with olefins whereby a particularly desired compound is obtained as a result of effecting the free-radical induced alkylation reaction in the presence of hydrogen chloride.

Heretofore, it has been known to condense alkyl halides with unsaturated hydrocarbons and particularly olefinic hydrocarbons or halogenated olefinic hydrocarbons in the presence of metal halide catalysts which are commonly known as Friedel-Crafts type catalysts. These catalysts will include aluminum chloride, aluminum bromide, zinc chloride, ferric chloride, zirconium chloride, etc. The reaction proceeds by addition of the alkyl group to one of the doubly-bonded carbon atoms of the olefin and the halogen atom to the other doubly-bonded carbon atom. In other words, the carbon-halogen bond of the alkyl halide is involved in the reaction. I have now discovered how to involve reaction of a carbon-hydrogen bond of an alkyl halide; that is, how to cause alkylation of the alkyl halide by the olefin by the addition of the haloalkyl group and a hydrogen atom of the alkyl halide across the double bond of the olefin. Such a reaction is completely new. For example: Previously known reaction:

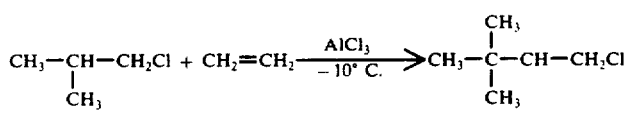

Reaction of the present invention:

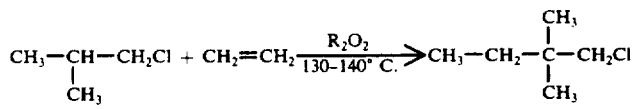

As was shown above, it was heretofore also known that the peroxide-induced reaction of ethylene with hydrogen chloride results in telomerization which produces n-alkyl chlorides possessing an even number of carbon atoms in the range of from 2 to about 20 carbon atoms or more. This reaction differs from the reaction of the present process because there is present much less alkyl chloride than ethylene which leads to the reaction of the ethylene first with itself, and then with the hydrogen chloride (i.e., telomerization) rather than reaction of the ethylene with alkyl chloride and then with hydrogen chloride (the alkylation reaction of the subject invention).

Alkyl halides of higher molecular weight than the original compounds which possess specific and particular configurations are useful intermediates in the preparation of many organic compounds or chemicals. Primary alkyl halides find many uses, for example, in the synthesis of flavors, perfumes, medicines, dyes and resins. In addition, they may also be converted to primary alcohols, primary amines, fatty acids, n-alkanesulfonic acids and other desirable compounds. Some higher molecular weight alkyl halides may be converted to hydrocarbons which are utilized as components of gasoline, the hydrocarbons which contain a highly branched-chain structure being utilized in the production of high-octane gasoline. In addition, a compound such as 1-chloro-2,2-dimethylbutane may be used in the preparation of pharmaceutical compounds including some compounds which may be useful as soporifics. Likewise, the amyl chlorides may be used in the synthesis of other amyl compounds; as solvents; as rotogravure ink vehicles; as rubber cements or in soil fumigation. Higher molecular weight alkyl and cycloalkyl halides find a large variety of uses.

It is therefore an object of this invention to provide a process for preparing higher molecular weight alkyl halides.

A further object of this invention is to provide a process for obtaining improved yields of desired products by reacting the process in the presence of certain catalytic compositions of matter and a promoter which comprises hydrogen chloride.

In one aspect an embodiment of this invention resides in an alkylation process which comprises reacting an olefin containing from 2 to about 9 carbon atoms with a halide reactant selected from the group consisting of a monohaloalkane containing from 3 to about 16 carbon atoms, monohalocycloalkane containing 5 or 6 carbon atoms in the ring and an aralkyl monohalide containing from 2 to about 4 carbon atoms in the alkyl group, said halide reactant containing at least one aliphatic carbon atom which possesses at least one hydrogen atom, said reaction being effected in the presence of a catalytic system consisting essentially of hydrogen chloride and a free-radical generating organic peroxide compound, at reaction conditions which include a temperature in the range of from about 50° to about 300° C. and at least as high as the decomposition temperature of said organic peroxide compound and a pressure of from about atmospheric to about 100 atmospheres, and recovering the resultant alkylated halide product.

A specific embodiment of this invention is found in a process for the alkylation of a monohaloalkane which comprises treating n-butyl chloride with ethylene in the presence of a catalyst system consisting essentially of hydrogen chloride and di-t-butyl peroxide at a temperature in the range of from about 50° to about 300° C. and at least as high as the initial decomposition temperature of said di-t-butyl peroxide and a pressure in the range of from about atmospheric to about 100 atmospheres, and recovering the resultant chlorohexanes and chlorooctanes.

Other objects and embodiments will be found in the following further detailed description of the present invention.

As hereinbefore set forth the present invention is concerned with a process for the alkylation of organic halides whereby improved yields of the desired products are obtained, the improvement in the yield being afforded by the use of a promoter of the type hereinafter set forth in greater detail. The organic halides which may be alkylated according to the process of this invention will include monohaloalkanes, monohalocycloalkanes and aralkyl monohalides, the halogen-containing compound is characterized by the presence of at least one aliphatic carbon atom which possesses a hydrogen atom. The term alkyl halides as used in the present specification will include both monohaloalkanes and monohalocycloalkanes. The preferred monohaloalkanes which are used as one of the starting materials in the present process are those which contain at least one carbon atom, other than the one which possesses the halogen atom which is a secondary or tertiary carbon atom (i.e., possesses at least one hydrogen atom). Specific examples of these alkyl halides or monohaloalkanes which contain from 3 to about 16 carbon atoms in which the preferred halogen comprises chlorine, bromine or fluorine will include n-propyl chloride, n-propyl bromide, n-propyl fluoride, isopropyl chloride, isopropyl bromide, isopropyl fluoride, 1-chlorobutane, 1-bromobutane, 1-fluorobutane, isobutyl chloride, isobutyl bromide, isobutyl fluoride, 1-chloropentane, 1-bromopentane, 1-fluoropentane, 1-chlorohexane, 1-bromohexane, 1-fluorohexane, 1-chloroheptane, 1-bromoheptane, 1-fluoroheptane, 1-chlorooctane, 1-bromooctane, 1-fluorooctane, 1-chlorononane, 1-bromononane, 1-fluorononane, 1-chlorodecane, 1-bromodecane, 1-fluorodecane, 1-chloroundecane, 1-bromoundecane, 1-fluoroundecane, 1-chlorododecane, 1-bromododecane, 1-fluorododecane, 1-chlorotridecane, 1-bromotridecane, 1-fluorotridecane, 1-chlorotetradecane, 1-bromotetradecane, 1-fluorotetradecane, 1-chloropentadecane, 1-bromopentadecane, 1-fluoropentadecane, 1-chlorohexane, 1-bromohexadecane, 1-fluorohexadecane, 1-chloro-2-methylpentane, 1-bromo-2-methylpentane, 1-fluoro-2-methylpentane, 1-chloro-3-methylpentane, 1-bromo-3-methylpentane, 1-fluoro-3-methylpentane, 1-chloro-2-methylhexane, 1-bromo-2-methylhexane, 1-fluoro-2-methylhexane, 1-chloro-3-methylhexane, 1-bromo-3-methylhexane, 1-fluoro-3-methylhexane, 1-chloro-4-methylhexane, 1-bromo-4-methylhexane, 1-fluoro-4-methylhexane, 1-chloro-4-methylheptane, 1-bromo-4-methylheptane, 1-fluoro-4-methylheptane, 1-chloro-3,3-dimethylhexane, 1-bromo-3,3-dimethylhexane, 1-fluoro-3,3-dimethylhexane, 1-chloro-3,3-dimethylheptane, 1-bromo-3,3-dimethylheptane, 1-fluoro-3,3-dimethylheptane, 1-chloro-3,3-dimethyloctane, 1-bromo-3,3-dimethyloctane, 1-fluoro-3,3-dimethyloctane, 2-chlorobutane, 2-bromobutane, 2-fluorobutane, 2-chloropentane, 2-bromopentane, 2-fluoropentane, 2-chlorohexane, 2-bromohexane, 2-fluorohexane, 2-chloroheptane, 2-bromoheptane, 2-fluoroheptane, 2-chlorooctane, 2-bromooctane, 2-fluorooctane, 2-chlorononane, 2-bromononane, 2-fluorononane, 2-chlorodecane, 2-bromodecane, 2-fluorodecane, the corresponding undecanes, dodecanes, tridecanes, tetradecanes, pentadecanes, hexadecanes, and 3-halo- and more internally substituted alkyl halides, etc.; aralkyl monohalides containing from 2 to about 4 carbon atoms in the alkyl group such as benzyl chloride, benzyl bromide, beta-phenylethyl chloride, gamma-phenylpropyl chloride, delta-phenylbutyl chloride, beta-phenylethyl bromide, gamma-phenylpropyl bromide, delat-phenylbutyl bromide, beta-phenylethyl fluoride, gamma-phenylpropyl fluoride, delta-phenylbutyl fluoride, 1-(chloromethyl)-naphthalene, 2-(chloromethyl)naphthalene, 1-(beta-chloroethyl)naphthalene, 1-(gamma-chloropropyl)-naphthalene, 2-(beta-chloroethyl)naphthalene, 2-(gamma-chloropropyl)naphthalene, diphenylmethyl chloride, etc.; monohalocycloalkanes containing 5 or 6 carbon atoms in the ring such as cyclopentyl chloride, cyclopentyl bromide, cyclopentyl fluoride, cyclohexyl chloride, cyclohexyl bromide, cyclohexyl fluoride, 1-chloro-1-methylcyclopentane, 1-bromo-1-ethylcyclohexane, (2-chloroethyl)cyclohexane, etc. The preferred aralkyl monohalides which are utilized in this process comprise omega-haloalkyl arenes inasmuch as these compounds are the most readily available compounds. However, it is also contemplated within the scope of this invention that other aralkyl monohalides such as (1-chlorethyl)benzene, (1-bromoethyl)benzene, (1-chloropropyl)benzene, (2-chloropropyl)benzene, (2-bromopropyl)benzene, (2-chlorobutyl)benzene, (3-bromobutyl)benzene, (1-chloroethyl)naphthalenes, (2-chloropropyl)naphthalenes, (1-bromoethyl)naphthalenes, (2-bromopropyl)-naphthalene, etc., may also be used although not necessarily with equivalent results.

Suitable unsaturated hydrocarbons or olefins which may be employed as the alkylating agent by condensation with the aforementioned organic halides will include in particular olefinic hydrocarbons containing from 2 to about 9 carbon atoms such as ethylene, propylene, 1-butene, 2-butene, 1-pentene, 2-pentene, 1-hexene, 2-hexene, 3-hexene, 1-heptene, 2-heptene, 3-heptene, 1-octene, 2-octene, 3-octene, 4-octene, 1-nonene, 2-nonene, 3-nonene, 4-nonene, etc., cyclopentene, cyclohexene, etc. It is to be understood that the aforementioned organic halides and olefins are only representative of the class of compounds which may be used and that the present invention is not necessarily limited thereto. Straight chain 1-alkenes are in general a preferred class of olefinic hydrocarbons; ethylene is the generally preferred 1-alkene. Tertiary olefins are generally the least preferred class because of the polymerization side reaction they can undergo.

The alkylation of the aforementioned monohaloalkanes, monohalocycloalkanes or aralkyl monohalides with an olefinic hydrocarbon of the type hereinbefore set forth is effected in the presence of certain catalytic compositions of matter comprising a promoter (hydrogen chloride, hereinafter described) and a catalyst, namely a compound which will generate free radicals at the conditions of temperature and pressure under which the present reaction takes place. Examples of these catalysts will include in particular organic peroxy compounds containing the bivalent radical -O-O- which is capable of inducing the condensation reaction. The organic compounds which constitute a preferred class of catalysts for use in this invention will include peracetic acid, persuccinic acid, dimethyl peroxide, diethyl peroxide, dipropyl peroxide, di-t-butyl peroxide, butyryl peroxide, lauroyl peroxide, benzoyl peroxide, tetrahydronaphthalene peroxide, urea peroxide, t-butyl perbenzoate, t-butyl hydroperoxide, methylcyclohexyl hydroperoxide, cyclohexanone peroxide, cumene hydroperoxide, etc. It is also contemplated within the scope of this invention that organic peroxy compounds which are compounded commercially with various diluents for use as free-radical generating agents may be used and will include benzoyl peroxide compounded with calcium sulfate, benzoyl peroxide compounded with camphor, etc. Only catalytic amounts (less than stoichiometric amounts) are needed.

The reaction of the present process involving the aforementioned starting materials is effected at elevated reaction temperatures which should be at least as high as the initial decomposition temperature of the free-radical generating catalysts, such as the peroxide compound, in order to form and liberate free radicals which promote the reaction. In selecting a particular reaction temperature for use in the process of the present invention, two considerations must be taken into account. First, sufficient energy by means of heat must be supplied to the reaction system so that the reactants, namely, the organic halide and the unsaturated hydrocarbon, will be activated sufficiently for radical transfer to take place when free radicals are generated by the catalyst. Second, free-radical generating catalysts such as peroxy compounds, particularly organic peroxides, decompose at a measurable rate with time in a logarithmic function dependent upon temperature. This rate of decomposition can be and ordinarily is expressed as the half life of a peroxide at a particular temperature. For example, the half life in hours for di-t-butyl peroxide is 17.5 hours at 125° C., 5.3 hours at 135° C. and 1.7 hours at 145° C. (calculated from data for the first 33% decomposition). A reaction system temperature must then be selected so that the free-radical generating catalyst decomposes smoothly with the generation of free radicals at a half life which is not too long. In other words, sufficient free radicals must be present to induce the present chain reaction to take place, and these radicals must be formed at a temperature at which the reactants are in a suitably activated state for conversion. When the half life of the free-radical generating catalyst is greater than 10 hours, radicals are not generated at a sufficient rate to cause the reaction to go forward at a sufficiently detectable rate. Thus, the reaction temperature may be within the range of from about 50° to about 300° C. and at least as high as the decomposition temperature of the catalyst, by which is meant a temperature such that the half life of the free-radical generating catalyst is not greater than 10 hours. Since the half life for each free-radical generating catalyst is different at different temperatures, the exact temperature to be utilized in a particular reaction will vary. However, persons skilled in the art are well acquainted with the half life vs. temperature data for different free-radical generating catalysts and thus, it is within the skill of one familiar with the art to select the particular temperature needed for any particular catalyst. However, the operating temperatures generally do not exceed the decomposition temperature of the catalyst by more than about 150° C. For example, when a free-radical generating catalyst such as t-butyl perbenzoate is used having a decomposition temperature of approximately 115° C., the operating temperature of the process is from 115° to about 265° C. When di-t-butyl peroxide having a decomposition temperature of about 130° C. is used, the process is run at a temperature ranging from about 130° to about 280° C. Higher reaction temperatures may be employed, but little advantage is gained if the temperature is more than the hereinbefore mentioned 150° C. higher than the decomposition temperature of the catalyst.

In addition to the elevated temperatures which are utilized, the reaction may also be effected at elevated pressures ranging from about 1 to about 100 atmospheres or more, the preferred operating pressure of the process being that which is required to maintain a substantial portion of the reactants in liquid phase. Pressure is not an important variable in the process of this invention. However, because of the low boiling points of some of the reactants, it is necessary to utilize pressure-withstanding equipment to insure liquid phase conditions. In batch type operations, it is often desirable to utilize pressure-withstanding equipment to charge the reactants and catalysts to the vessel, and to pressure the vessel with 10, 30 or 50 or more atmospheres with an inert gas such as nitrogen. This helps to insure the presence of liquid phase conditions. However, when the molar quantity of reactants is sufficient, the pressure which they themselves generate at the temperature utilized is sufficient to maintain the desired phase conditions.

As hereinbefore set forth and as will hereinafter be shown in the examples which will be found at the end of the specification, it is possible to obtain improved yields of the desired products by effecting the alkylation of the monohaloalkane, monohalocycloalkane or aralkyl monohalide with the olefin in the presence of a free-radical generating compound and a promoter, said promoter comprising hydrogen chloride. This will in effect form a catalyst system, said catalyst system consisting essentially of the free-radical generating compound and hydrogen chloride promoter. The promoter may be added or present in the reaction mixture in the form of gaseous hydrogen chloride, dilute hydrochloric acid or concentrated (about 38%) hydrochloric acid. It may be added to the reaction mixture before or after adding the olefin.

The process of this invention may be effected in any suitable manner and may comprise either a batch or continuous type operation. For example, when a batch type operation is used, a quantity of the monohaloalkane, monohalocycloalkane or aralkyl monohalide, the catalyst and the hydrogen chloride, if in a liquid form, are placed in an appropriate condensation apparatus. A particularly suitable type of apparatus for this reaction comprises an autoclave of the rotating or mixing type. A glass liner containing the monohaloalkane, monohalocycloalkane, aralkyl monohalide, peroxide and promoter is sealed into the autoclave and the olefin, if in gaseous form, is added thereto. Thereafter the apparatus and contents thereof are heated to the desired operating temperature which is at least as high as the decomposition temperature of the free-radical generating compound and preferably not greater than 150° C. higher than said decomposition temperature. If the olefin is in gaseous form, it may provide the autogenous pressure which is necessary to effect the reaction in a liquid phase. However, it is also contemplated within the scope of this invention that the olefin in a gaseous state may provide only a partial pressure of the total operating pressure, the remainder of said pressure being provided for by the introduction of a substantially inert gas such as nitrogen into the reaction zone. After maintaining the apparatus and contents thereof at the desired operating conditions of temperature and pressure for a predetermined residence time which may range from about 0.5 up to about 10 hours or more in duration, heating is discontinued and the vessel and contents thereof are allowed to cool to room temperature. The excess pressure is vented, the apparatus is opened and the reaction mixture is recovered therefrom. The reaction mixture may then be subjected to conventional means of separation and purification including, but not limited to, extraction, washing, drying, fractional distillation, etc., whereby the desired high molecular weight monohaloalkane, monohalocycloalkane or aralkyl monohalide is separated and recovered from any unreacted starting materials and/or undesired side reaction products which may have been formed during the reaction.

It is also contemplated within the scope of this invention that the process described may be effected in a continuous manner of operation. When such a type of operation is used, the starting material comprising the monohaloalkane, monohalocycloalkane, or aralkyl monohalide and the olefin are continuously charged to a reaction zone which is maintained at the proper operating conditions of temperature and pressure. In addition, the particular free-radical generating compound which acts as a catalyst for the reaction and hydrogen chloride (anhydrous or in aqueous solution) are also continuously charged thereto. The reactants and the catalyst plus promoter may be charged through separate lines or, if so desired, they may be admixed prior to entry into said reactor and charged thereto in a single stream. Upon completion of the desired residence time, the reactor effluent is continuously withdrawn and subjected to conventional means of separation of the type hereinbefore set forth whereby the desired higher molecular weight monohaloalkanes, monohalocycloalkanes or aralkyl monohalides are recovered while any unreacted starting materials may be recycled to form a portion of the feed stock.

The following examples are given to illustrate the process of the present invention which, however are not intended to limit the generally broad scope of the present invention in strict accordance therewith.

EXAMPLE I

In this example 73 grams (0.79 mole) of n-butyl chloride along with 6 grams of di-t-butyl peroxide and 24 grams of concentrated hydrochloric acid were placed in the glass liner of a rotating autoclave. The glass liner was sealed into the autoclave and ethylene charged to the reactor until an initial operating pressure of 20 atmospheres was reached. In addition, nitrogen was also pressed in until the operating pressure reached 40 atmospheres, said 40 atmospheres consisting of 20 atmospheres of nitrogen and 20 atmospheres of ethylene. The reactor was then heated to a temperature of 130° C. and maintained in a range of from 130° to 140° C. for a period of 4 hours, the maximum pressure during this period reached 56 atmospheres. At the end of this 4-hour period, heating was discontinued and the autoclave was allowed to return to room temperature, the final pressure at room temperature being 32 atmospheres. The excess pressure was discharged, the autoclave was allowed to return to room temperature, the final pressure at room temperature being 32 atmospheres. The excess pressure was discharged, the autoclave was opened and 106 grams of reaction product was recovered. The product was subjected to conventional means of separation of the upper organic layer from the lower aqueous layer followed by washing with water, drying and fractional distillation whereby 18 grams of product boiling chiefly in a range of from 110° to 150° C. was submitted to preparative gas chromatography followed by instrumental analyses. Six eluted peaks were observed in the following relative areas (weight percent): (1) 20; (2) 40; (3) 5; (4) 5; (5) 8; and (6) 22.

In peak 1 the infrared spectrum of the peak was that of an alkyl chloride. A secondary chloride was indicated by the fact that the CCl was at 660 cm$^{-1}$ and 610 cm$^{-1}$. The CCl bands matched those reported for 3-chlorohexane. The mass spectroscopy spectrum had isotopic peaks at m/e 35, 36, 37 and 38 indicating the presence of chlorine. The most abundant ion in the mass spectrum was at m/e 55 which corresponded to a $C_4$ alkene fragment ion, An important ion was observed at m/e 85 corresponding to a hexyl ion formed by dechlorination of 3-chlorohexane; beta-scission of the ion yielded the $C_4$ fragment ion. In addition, nuclear magnetic resonance confirmed that the chlorine atom in the alkyl chloride of peak 1 was present as a secondary chloride.

The infrared spectrum of peak 2 was that of an alkyl chloride. Absorption at 660 cm$^{-1}$ for CCl indicated that $RCH_2CH_2Cl$ was probable. In addition a single band at 1380 cm$^{-1}$ for $CH_3$ indicated that no isopropyl-type $CH_3$'s were present. In addition, mass spectroscopy again indicated the presence of chlorine and nuclear magnetic resonance showed that peak 2 was a primary alkyl chloride with a significant amount of methyl group. There were two hydrogen atoms attached to a primary carbon atom and 6 hydrogen atoms attached to primary methyl groups. In addition there were 5 hydrogen atoms involved in other —$CH_2$— and ═CH— groups. The analytical data indicated that the structure was 1-chloro-3-methylpentane.

The infrared and mass spectrum of peak 3 matched the reference spectrums for 1-chlorohexane.

The infrared spectrum of peak 4 indicated that this was an alkyl chloride which was very similar to the compound of peak 1. The CCl band was at 610 cm$^{-1}$ and 665 cm$^{-1}$. A single band for —$CH_3$ at 1385 cm$^{-1}$ indicated that there were no isopropyl methyls. The most abundant ion in the mass spectrum of material was at m/e 55 corresponding to a $C_4$ alkane fragment ion, while ion peaks at m/e 56 and 57 were also very prominent which suggested that a butyl group was lost quite readily from the parent ion. The highest m/e detected was a small isotopic cluster at m/e 148-150 which corresponds to a chlorooctane. The data thus obtained indicated that the sample was a mixture of octyl chlorides, the data fitting a number of secondary octyl chlorides.

The gas chromatography of peak 5 indicated that said peak consisted of at least two components, the infrared spectrum indicating the presence of secondary alkyl chlorides while the mass spectrum indicated that one of the two peaks making up peak 5 appears to be a branched octyl chloride. The data again indicated that there was a mixture of octyl chlorides present.

Peak 6 appeared to be due to a mixture of at least 3 components, infrared again indicating the presence of alkyl chlorides, while the CCl at 660 cm$^{-1}$ indicated a primary chloride. The most prominent ion in the mass spectrum of the sample was at m/e 43 which corresponds to $C_3H_7^+$. In addition, loss of ethyl at m/e 29 and ethane at m/e 30 was noted. The nuclear magnetic resonance integral values indicated that the peak was a mixture of primary and secondary alkyl chlorides. A possible structure which fits the mass spectrum data is 3-chloro-3-ethylhexane.

It may be concluded that the major product of the ethylation of n-butyl chloride is 1-chloro-3-methylpentane formed by alkylation at the penultimate carbon atom of the chloride; the next most prominent hexyl chloride is 3-chlorohexane formed by ethylation at the primary carbon atoms holding the chlorine atom.

EXAMPLE II

To illustrate the necessity for the presence of hydrogen chloride in the reaction mixture, another experiment was run in which 73 grams (0.79 mole) of n-butyl chloride along with 6 grams of di-t-butyl peroxide was placed in the glass liner of a rotating autoclave. The liner was sealed into the autoclave and 0.8 mole of ethylene was pressed in along with nitrogen so that an initial operating pressure of 40 atmospheres consisting of 20 atmospheres of ethylene and 20 atmospheres of nitrogen was reached. The autoclave was then heated to a temperature of 130° C. and maintained in a range of from 130° to 140° C. for a period of 4 hours, the maximum pressure at this temperature reaching 54 atmospheres. At the end of the 4-hour period, heating was discontinued and the autoclave allowed to return to room temperature, the final pressure at room temperature being 38 atmospheres. The excess pressure was discharged and the autoclave was opened. However, it was determined that little reaction had occurred and no alkylated product was obtained.

It is therefore readily apparent from a comparison of the two experiments that the presence of hydrogen chloride is necessary when alkylating a monohaloalkane, monohalocycloalkane or aralkyl monohalide with an olefin in the presence of a free-radical generating compound.

EXAMPLE III

In this example 46 grams of 1-chloro-2-methylpropane (isobutyl chloride), 6 grams of di-t-butyl peroxide, 21 grams of concentrated hydrochloric acid and 21 grams of water were weighed into a glass liner which was then sealed into a rotating autoclave. Ethylene was charged until the pressure reached 20 atmospheres, following which nitrogen was pressed in until the pressure reached 40 atmospheres (that is, 20 atmospheres of nitrogen were added). The autoclave was then heated (while rotating) to a temperature of 130° C. and maintained in the range of from 130° to 140° C. for 4 hours, the maximum pressure during this period reaching 62 atmospheres. Heating was discontinued and the autoclave was permitted to cool to room temperature at which temperature the final pressure was 38 atmospheres. The excess pressure was discharged, the autoclave was opened and 91 grams of product was recovered. The upper layer was separated from the lower layer, washed with water, dried over potassium carbonate and fractionally distilled. Product boiling chiefly at 115°–130° C. (about 7 grams) was submitted to preparative gas chromatography followed by instrumental analysis of the peaks. Five product peaks were present in the following approximate ratios: (1) 65; (2) 12; (3) 9; (4) 9 and (5) 5.

The infrared spectrum of peak 1 indicated that it was due to an alkyl chloride. A strong CCl band at 750 cm$^{-1}$ indicated gem-dimethyl and at least one other methyl. 1-Chloro-2,2-dimethylbutane is supported by these data and also by the mass spectrum which showed a chlorine isotope cluster at m/e 105, 107, corresponding to loss of a methyl from $C_6H_{13}Cl$ and another at m/e 91, 93, corresponding to loss of ethyl from $C_6H_{13}Cl$. The most abundant peak at m/e 71 corresponded to $C_5H_{11}$ formed by the loss of chloromethyl.

The infrared spectrum of peak 2 indicated an alkyl chloride, bands at 690 cm$^{-1}$ and 730 cm$^{-1}$ (CCl) indicated a primary alkyl chloride while a single band at 1380 cm$^{-1}$ indicated methyls which were not gem-dimethyls or in a t-butyl group. These observations suggested 1-chloro-2-methylpentane as did the mass spectrum. In the latter, the most abundant ion was m/e 43 indicating the presence of a propyl group. A chlorine isotope cluster at m/e 120, 122 suggested that the compound was a $C_6H_{13}Cl$, confirmed by loss of HCl yielding m/e 84 corresponding to $C_6H_{12}$. The second most abundant ion was at m/e 71 corresponding to $C_5H_{11}$ formed by elimination of chloromethyl from the parent ion.

Peak 3's infrared spectrum showed that it was an alkyl chloride having CCl bands at 620 and 660 cm$^{-1}$ indicating a secondary alkyl chloride. The methyl band at 1380 cm$^{-1}$ showed shoulders suggesting the presence of isopropyl methyls. These data combined with the mass spectrum interpretation indicated 3-chloro-2-methylpentane. The highest significant ion in the mass spectrum was a low abundance chlorine isotope cluster at m/e 120, 122 (i.e., $C_6H_{13}Cl$). Loss of HCl from the parent ion was indicated since the corresponding alkene was observed at m/e 84. The three most abundant ions were m/e 43, 42 and 41 indicating the presence of a propyl group in the compound. An ion at m/e 76, 78, corresponding to $C_3H_5Cl$ was also observed.

The infrared and the mass spectra of peak 4 matched reference spectra of 1-chlorohexane, formation of which probably involved telomerization on ethylene with hydrogen chloride.

The highest m/e value in the mass spectrum of peak 5 was at m/e 133, 135 corresponding to $C_7H_{14}Cl^+$. This seemed to be a fragment ion produced by the loss of a methyl group from $C_8H_{17}Cl$, the presence of which was suggested by the observed fragment ion corresponding to $C_8H_{16}$ formed by loss of HCl from the unobserved parent ion. The most abundant ion was at m/e 57 indicating the presence of a butyl group. A very prominent ion was also observed at m/e 99 ($C_7H_{15}^+$) corresponding to loss of chloromethyl. The data support either 1-chloro-2,2-dimethylhexane or 1-chloro-2,2,3-trimethylpentane. The latter would tend to show a significant loss of methyl and some loss of ethyl groups. Since little methyl or ethyl loss was observed, the compound was probably 1-chloro-2,2-dimethylpentane formed by further reaction with ethylene of the intermediate responsible for the formation of the most abundant product, peak 1.

It may be concluded that the ethyl group is introduced most readily at the tertiary carbon atom of isobutyl chloride, next most readily at the primary carbon atom to which are attached 3 hydrogen atoms and least readily at the primary carbon atom holding 2 hydrogen atoms and 1 chlorine atom.

It will be noted that the product which is obtained by alkylating isobutyl chloride with ethylene in the presence of di-t-butyl peroxide and hydrogen chloride is largely 1-chloro-2,2-dimethylbutane. This differs from the product which was obtained by alkylating isobutyl chloride with ethylene in the presence of aluminum chloride, these reactions being hereinbefore described by two sets of equations found in the section "Background of the Invention", wherein the principal product comprised 1-chloro-2,2-dimethylbutane when peroxide was used, and 1-chloro-3,3-dimethylbutane when aluminum chloride was used.

EXAMPLE IV

In this example 52 grams of 1-chloro-3-methylbutane (isopentyl chloride) along with 6 grams of di-t-butyl peroxide, 21 grams of concentrated hydrochloric acid and 21 grams of water were placed in the glass liner of a rotating autoclave. The liner was sealed into the autoclave and 0.6 mole of ethylene along with a sufficient amount of nitrogen was pressed into the autoclave until an initial operating pressure of 40 atmospheres consisting of 20 atmospheres of nitrogen and 20 atmospheres of ethylene was reached. The autoclave was then heated to a temperature of 130° C. and maintained in a range of from 130° to 140° C. for a period of 4 hours, the maximum pressure at this temperature reaching 49 atmospheres. At the end of the aforementioned 4-hour period, heating was discontinued and the autoclave allowed to return to room temperature, the final pressure at room temperature being 32 atmospheres. The excess pressure was discharged, the autoclave was opened and the reaction mixture recovered therefrom. The upper layer was separated from the lower aqueous layer, water washed, dried and subjected to fractional distillation. The cuts boiling at 148° to 181° C. were recovered, combined and submitted to preparative gas chromatography followed by instrumental analysis. The chromatography analysis disclosed that there was one major peak and at least five minor peaks.

The infrared spectrum of peak 1 indicated that the product was a secondary alkyl chloride inasmuch as it had adsorptions at 610 and 665 cm$^{-1}$. The highest significant ion detected in the mass spectrum of the example was m/e 98 which corresponded to $C_7H_{14}$. Isotope calculations and a low ionizing voltage mass spectrum indicated that it was probably not the parent ion. Small isotopic peaks at m/e 34, 36, 37 and 38 indicated the presence of chlorine although no major fragment ion containing chlorine was observed. An abundant ion was noted at m/e 56 indicating the loss of a $C_4$ alkene from the parent ion. The ion observed at m/e 98 appeared to have been formed by the loss of hydrogen chloride from the parent ion thereby showing that the material was a heptyl chloride. A compound which fits the observed data is 4-chloro-2-methylhexane formed by the ethylation at the carbon atom holding the chlorine atom.

The analysis of peak 2 showed that it was a mixture of compounds, the major one being 1-chlorohexane with suggestions that other components such as small amounts of hexenes and heptenes were probably also present.

Analysis of peak 3 (the major peak) indicated that this was a mixture of compounds. The infrared spectrum indicated that the major component was an alkyl chloride with methyl bands at 1365, 1380 and 1388 cm$^{-1}$, thus suggesting a gem-dimethyl group and another methyl. The mass spectrum indicated that the highest significant peak was a chlorine isotope cluster at m/e 119 and 121 containing one chlorine atom. Prominent ions were observed at m/e 69 and 71 indicating that a $C_5$ fragment ion was easily formed. Since the isotopic cluster at m/e 119 and 121 corresponded to $C_6H_{12}Cl^+$, the parent ion was at least a $C_7$ chloride. A structure which fits the above observation for peak 3 is 1-chloro-3,3-dimethylpentane formed by ethylation at the tertiary carbon atom.

Both the infrared and mass spectrum analysis of peak 4 indicated the presence of an alkyl chloride and an olefin, the mass spectrum indicating that these were $C_9H_{19}Cl$ and $C_9H_{18}$. In addition, the mass spectrum found that the highest significant ion was a fragment ion isotopic cluster at m/e 147 and 149 corresponding to $C_8H_{16}Cl^+$. The most abundant ion was observed at m/e 97 corresponding to $C_7H_{13}^+$. This indicated that a chlorine which fits the above data for peak 4 is chloro-3-methyloctane.

Mass spectrum of peak 5 indicated that the most significant ion detected in this peak was observed at m/e 119 and 121 which corresponds to $C_6H_{12}Cl^+$. A prominent ion at m/e 77, 79 corresponded to $C_3H_6Cl^+$.

Infrared spectrum of peak 6 disclosed evidence for a primary chloride (CCl at 655 cm$^{-1}$). Mass spectrum analysis of this peak disclosed that the highest m/e value was 147, 149, a chlorine isotopic cluster which corresponds to $C_8H_{16}Cl^+$. The most abundant ion was m/e 69 corresponding to $C_5H_9^+$. Other prominent ions which were observed in the mass spectrum of the sample were m/e 57 ($C_4H_9^+$) and m/e 99 ($C_7H_{15}^+$). In addition, a rearrangement ion was observed at m/e 104, 106 corresponding to $C_5H_9Cl$. It was concluded from these analyses that the peak was due to a chlorononane.

EXAMPLE V

In this example 61 grams (0.8 mole) of n-butyl fluoride along with 6 grams of di-t-butyl peroxide and 24 grams of concentrated hydrochloric acid are placed in the glass liner of a rotating autoclave. The liner is sealed into the autoclave and 0.6 mole of propylene is charged thereto. In addition, a sufficient amount of nitrogen is also pressed into the autoclave so that an initial operating pressure of 40 atmospheres consisting of 20 atmospheres of propylene and 20 atmospheres of nitrogen is reached. The autoclave is then heated to a temperature of 130° C. and maintained in a range of from 130° to 140° C. for a period of 4 hours. At the end of this time, heating is discontinued and the autoclave is allowed to return to room temperature. The excess pressure is discharged, the autoclave is opened, and the reaction product is recovered therefrom. The upper organic layer is separated from the lower aqueous layer, washed, dried and subjected to fractional distillation under reduced pressure whereby the desired cuts are recovered therefrom. Analysis of these cuts will disclose the presence of a mixture of fluoroheptanes and fluorodecanes.

EXAMPLE VI

A mixture consisting of 121 grams (0.8 mole) of n-amyl bromide, 6 grams of di-t-butyl peroxide and 25 grams of concentrated hydrochloric acid is placed in the glass liner of a rotating autoclave which is thereafter sealed into said autoclave. A sufficient amount of ethylene and nitrogen are pressed into the autoclave so that an initial operating pressure of 40 atmospheres (20 atmospheres of ethylene and 20 atmospheres of nitrogen) is reached. The autoclave is heated to a temperature of 130° C. and maintained thereat for a period of 6 hours. At the end of the aforementioned 6-hour period, heating is discontinued, the autoclave is allowed to return to room temperature and the excess pressure is discharged. After opening the autoclave, the reaction mixture is recovered and the upper organic layer is separated from the lower aqueous layer. The organic layer is washed, dried and subjected to fractional distillation under reduced pressure. The desired cuts are recovered from this distillation and subjected to preparative gas chromatography analysis. The peaks which are found in this analysis are further analyzed by means of infrared, nuclear magnetic resonance and mass spectroscopy which will indicate the presence of a mixture of bromoheptanes and bromononanes.

EXAMPLE VII

Alkylation also took place when a secondary or a tertiary alkyl chloride was heated at 130°-140° C. under ethylene pressure in the presence of di-t-butyl peroxide and concentrated hydrochloric acid using the procedure described in Example I. At least two isomeric heptyl chlorides were produced by the ethylation of 2-chloropentane and a hexyl chloride was formed from tert-butyl chloride.

EXAMPLE VIII

In this example a mixture comprising 119 grams of cyclohexyl chloride, 6 grams of di-t-butyl peroxide and 30 grams of concentrated hydrochloric acid is placed in the glass liner of a rotating autoclave. The liner is sealed into the autoclave and a mixture of 20 atmospheres of ethylene and 20 atmospheres of nitrogen is pressed in so that an initial operating pressure of 40 atmospheres is reached. Thereafter the autoclave is heated to a temperature of 130° C. and maintained in a range of from 130° to 140° C. for a period of 4 hours. Following this 4-hour period, heating is discontinued and the autoclave is allowed to return to room temperature. The excess pressure is discharged, the autoclave is opened, and the reaction mixture is recovered. The upper organic layer of the reaction mixture is separated from the lower aqueous layer, washed, dried and subjected to fractional distillation under reduced pressure, the desired cuts being recovered therefrom. The cuts which have been recovered from the distillation are subjected to preparative gas chromatography. This analysis will indicate that the product comprises a mixture of ethylcyclohexyl chlorides, the chief components being 3-chloroethylcyclohexane and 4-chloroethylcyclohexane.

EXAMPLE IX

A mixture consisting of 93 grams of beta-phenylethyl chloride [or (beta-chloroethyl)benzene as it may also be named], 7 grams of benzoyl peroxide and 30 grams of concentrated hydrochloric acid is placed in the glass liner of a rotating autoclave. The liner is sealed into the autoclave and a mixture of ethylene and nitrogen is pressed in until an initial operating pressure of 40 atmospheres consisting of 20 atmospheres of nitrogen and 20 atmospheres of ethylene is reached. The autoclave is then heated to a temperature of 80° C. and maintained in a range of from 80° to 100° C. for a period of 6 hours. At the end of this 6-hour period, heating is discontinued, the autoclave is allowed to return to room temperature and the excess pressure is discharged. After opening the autoclave, the reaction mixture is recovered and the organic upper layer is separated from the lower aqueous layer. The upper organic layer is treated in a manner similar to that set forth in the above examples, analysis of the desired cuts by means of infrared, mass spectroscopy and nuclear magnetic resonance disclosing the presence of a mixture of chiefly 1-chloro-2-phenylbutane and 1-chloro-2-phenylhexane.

I claim as my invention:

1. An alkylation process which comprises reacting an olefin containing from 2 to about 9 carbon atoms with a halide reactant selected from the group consisting of a monohaloalkane containing from 3 to about 16 carbon atoms, monohalocycloalkane containing 5 or 6 carbon atoms in the ring and an aralkyl monohalide containing from 2 to about 4 carbon atoms in the alkyl group, said halide reactant containing at least one saturated aliphatic carbon atom which possesses at least one hydrogen atom, said reaction being effected in the presence of a catalytic system consisting essentially of hydrogen chloride and a free radical-generating organic peroxide compound, at reaction conditions which include a temperature in the range of from about 50° to about 300° C. and at least as high as the decomposition temperature of said organic peroxide compound and a pressure of from about atmospheric to about 100 atmospheres, and recovering the resultant monoalkylated halide as the principal product.

2. The process as set forth in claim 1 in which said hydrogen chloride is in an aqueous solution.

3. The process as set forth in claim 1 in which said free-radical generating organic peroxide compound is di-t-butyl peroxide.

4. The process as set forth in claim 1 in which said free-radical generating organic peroxide compound is benzoyl peroxide.

5. The process as set forth in claim 1 in which said halide reactant is n-butyl chloride, said olefin is ethylene and said alkylated halide product is a mixture of chlorohexanes and chlorooctanes.

6. The process as set forth in claim 1 in which said halide reactant is n-butyl fluoride, said olefin is propylene and said alkylated halide product is a mixture of fluoroheptanes and fluorodecanes.

7. The process as set forth in claim 1 in which said halide reactant is n-amyl bromide, said olefin is ethylene and said alkylated halide product is a mixture of bromoheptanes and bromononanes.

8. The process as set forth in claim 1 in which said halide reactant is isobutyl chloride, said olefin is ethylene and said alkylated halide product is a mixture of chlorohexanes and chlorooctanes.

9. The process as set forth in claim 1 in which said halide reactant is cyclohexyl chloride, said olefin is ethylene and said alkylated halide product is a mixture of ethylcyclohexyl chlorides.

10. The process as set forth in claim 1 in which said halide reactant is beta-phenylethyl chloride, said olefin is ethylene and said alkylated halide product is a mixture of phenylbutyl chlorides and phenylhexyl chlorides.

11. The process as set forth in claim 1 in which said halide reactant is a monohaloalkane containing from 3 to about 16 carbon atoms.

12. The process as set forth in claim 1 in which said halide reactant is a monohalocycloalkane containing 5 or 6 carbon atoms in the ring.

* * * * *